US00PP23075P2

(12) United States Plant Patent
Conibear

(10) Patent No.: US PP23,075 P2
(45) Date of Patent: Sep. 25, 2012

(54) LUPINE PLANT NAMED 'GLADIATOR'

(50) Latin Name: ***Lupinus* hybrid**
Varietal Denomination: Gladiator

(75) Inventor: Sarah Frances Conibear, Bideford (GB)

(73) Assignee: Specialis Plants B.V., Oude Wetering (NL)

( * ) Notice: Subject to any disclaimer, the term of this patent is extended or adjusted under 35 U.S.C. 154(b) by 0 days.

(21) Appl. No.: 13/134,171

(22) Filed: May 31, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell

(74) *Attorney, Agent, or Firm* — C. A. Whealy

(57) ABSTRACT

A new and distinct cultivar of Lupine plant named 'Gladiator', characterized by its upright plant habit; vigorous growth habit; numerous large yellow and orange red bi-colored flowers arranged on dense terminal racemes.

2 Drawing Sheets

Botanical designation: *Lupinus* hybrid.
Cultivar denomination: 'GLADIATOR'.

BACKGROUND OF THE INVENTION

The present invention relates to a new and distinct cultivar of Lupine plant, botanically known as *Lupinus* hybrid and hereinafter referred to by the name 'Gladiator'.

The new Lupine plant is a product of a planned breeding program conducted by the Inventor in Devon, United Kingdom. The objective of the breeding program is to develop new uniform and freely flowering Lupine plants with large attractive flowers.

The new Lupine plant originated from an open-pollination in June, 2004 of a seedling selection of *Lupinus* hybrid identified as *Lupinus* Russell Hybrid Seedling WCL 032/99, not patented, as the female, or seed, parent with an unknown selection of *Lupinus* hybrid as the male, or pollen, parent. The new Lupine plant was discovered and selected by the Inventor in June, 2005 as a single flowering plant within the progeny of the stated open-pollination in a controlled environment in Devon, United Kingdom.

Asexual reproduction of the new Lupine plant by micro propagation in a controlled greenhouse environment in Hillegom, The Netherlands since March, 2009 has shown that the unique features of this new Lupine plant are stable and reproduced true to type in successive generations of asexual reproduction.

SUMMARY OF THE INVENTION

Plants of the new Lupine have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Gladiator'. These characteristics in combination distinguish 'Gladiator' as a new and distinct Lupine plant:

1. Upright plant habit.
2. Vigorous growth habit.

3. Numerous large yellow and orange red bi-colored flowers arranged on dense terminal racemes.
4. Good garden performance.

Plants of the new Lupine can be compared to plants of the female parent selection. Plants of the new Lupine differ from plants of the female parent selection primarily in plant growth habit and flower color.

Plants of the new Lupine can be compared to plants of *Lupinus* hybrid 'Manhattan Lights', disclosed in U.S. Plant Pat. No. 18,868. Plants of the new Lupine differ from plants of 'Manhattan Lights' in the following characteristics:

1. Plants of the new Lupine are shorter than plants of 'Manhattan Lights'.
2. Plants of the new Lupine and 'Manhattan Lights' differ in flower color as plants of 'Manhattan Lights' have burgundy and yellow-colored flowers.

Plants of the new Lupine can also be compared to plants of *Lupinus* hybrid 'Saffron', disclosed in U.S. Plant Pat. No. 18,802. Plants of the new Lupine differ from plants of 'Saffron' in the following characteristics:

1. Plants of the new Lupine are taller than plants of 'Saffron'.
2. Plants of the new Lupine and 'Saffron' differ in flower color as plants of 'Saffron' have yellow-colored flowers.

BRIEF DESCRIPTION OF THE PHOTOGRAPHS

The accompanying colored photographs illustrate the overall appearance of the new Lupine plant showing the colors as true as it is reasonably possible to obtain in colored reproductions of this type. Colors in the photographs may differ slightly from the color values cited in the detailed botanical description which accurately describe the colors of the new Lupine plant.

The photograph on the first sheet is a side perspective view of a typical flowering plant of 'Gladiator' grown in an outdoor nursery and placed in a container for the purposes of the photograph.

The photograph on the second sheet is a close-up view of a typical inflorescence of 'Gladiator'.

DETAILED BOTANICAL DESCRIPTION

The aforementioned photographs and following observations, measurements and values describe plants of the new Lupine grown during the early summer in outdoor nursery in Vogelenzang, The Netherlands and under cultural practices which closely approximate commercial Lupine production. During the production of the plants, day temperatures ranged from 16° C. to 30° C. and night temperatures ranged from 6° C. to 18° C. Plants were two years old when the photographs and the detailed description were taken. In the detailed description, color references are made to The Royal Horticultural Society Colour Chart, 2007 Edition, except where general terms of ordinary dictionary significance are used.

Botanical classification: *Lupinus* hybrid 'Gladiator'.

Parentage:

*Female, or seed, parent.*—*Lupinus* Russell Hybrid Seedling WCL 032/99, not patented.

*Male, or pollen, parent.*—Unknown selection of *Lupinus* hybrid, not patented.

Propagation:

*Type.*—By micro propagation.

*Time to initiate roots.*—About four to five days at 20° C.

*Time to produce a rooted young plant, summer.*—About five to six weeks at 15° C. to 17° C.

*Time to produce a rooted young plant, winter.*—About seven to eight weeks at 15° C. to 17° C.

*Root description.*—Thick, fleshy; creamy white to light brown in color.

*Rooting habit.*—Main tap root with low lateral branching; medium in density.

Plant description:

*Plant and growth habit.*—Upright plant habit; vigorous growth habit.

*Branching habit.*—Freely basal branching habit.

*Plant height.*—About 72.5 cm.

*Plant diameter* (*area of spread*).—About 51 cm.

Lateral branch description:

*Length.*—About 31.3 cm.

*Diameter.*—About 1.2 cm.

*Internode length.*—About 7.9 cm.

*Texture.*—Pubescent.

*Strength.*—Strong.

*Color.*—Between 144C and 145A.

Foliage description:

*Arrangement.*—Alternate, palmately compound with about eleven leaflets per leaf.

*Leaf length.*—About 18.6 cm.

*Leaf width.*—About 18.6 cm.

*Leaflet length.*—About 10.8 cm.

*Leaflet width.*—About 2.7 cm.

*Leaf shape.*—Orbicular.

*Leaflet shape.*—Oblanceolate.

*Leaflet apex.*—Broadly acute.

*Leaflet base.*—Cuneate.

*Leaflet margin.*—Entire.

*Leaflet texture, upper surface.*—Smooth, glabrous.

*Leaflet texture, lower surface.*—Sparsely pubescent.

*Leaflet venation pattern.*—Pinnate.

*Leaflet color.*—Developing leaflets, upper surface: Close to 143A to 143B. Developing leaflets, lower surface: Close to 139C. Fully expanded leaflets, upper surface: Close to N137D; venation, close to 144A to 144B. Fully expanded leaflets, lower surface: Close to 138A; venation, close to 138A to 138B.

*Leaf petiole.*—Length: About 17.7 cm. Diameter: About 4 mm. Texture, upper and lower surfaces: Smooth, glabrous. Color, upper and lower surfaces: Close to 144B.

Flower description:

*Flower appearance/arrangement.*—Single large papilionaceous flowers arranged in dense racemes; freely flowering habit with usually about 200 flowers developing per inflorescence; flowers face mostly outwardly.

*Natural flowering season.*—Continuous flowering from late spring through the summer in The Netherlands.

*Flower longevity.*—Flowers last about two weeks on the plant; flowers not persistent.

*Fragrance.*—Moderately fragrant; somewhat peppery.

*Inflorescence height.*—About 38.2 cm.

*Inflorescence diameter.*—About 6.8 cm.

*Flower diameter.*—About 1.2 cm by 2.4 cm.

*Flower length* (*height*).—About 2.1 cm.

*Flower buds.*—Length: About 1 cm. Diameter: About 8 mm. Shape: Ovate. Color: Close to 154D; towards the base, close to 39B; calyx, close to 143C.

*Petals.*—Quantity per flower: Flowers papilionaceous with an upper standard petal, two lateral petals and a lower keel of two united petals. Length: Upper standard petal: About 1.8 cm. Lateral petals: About 1.7 cm. Lower keel: About 1.3 cm. Width: Upper standard petal: About 2.1 cm. Lateral petals: About 1.2 cm. Lower keel: About 1.3 cm. Shape: Upper standard petal: Orbicular; convex. Lateral petals: Obovate; curved and concave. Lower keel: Ovate; curved and folded. Apex: Upper standard petal: Emarginate. Lateral petals: Rounded. Lower keel: Caudate. Margin, all petals: Entire. Texture, upper and lower surfaces, all petals: Smooth, glabrous. Color, when opening, upper surface: Upper standard petal: Close to 3A; towards the margins, close to 3B to 3C; towards the base, close to 35B to 35C. Lateral petals: Close to 39B. Lower keel: Close to 2D; apex, close to 177A. Color, when opening, lower surface: Upper standard petal: Between 3B and 4A; towards the margins, close to 35B to 35C. Lateral petals: Close to 39A. Lower keel: Close to 2D; apex, close to 177A. Color, fully opened, upper surface: Upper standard petal: Close to 3A; towards the margins, close to 3C; towards the base, close to 35B; with development, color towards the margins becomes closer to 7A to 7C. Lateral petals: Close to 35C; with development, color becomes closer to 51A to 51B. Lower keel: Close to 195C; towards the apex, close to 176A; apex, close to 177A; color does not change with development. Color, fully opened, lower surface: Upper standard petal: Close to 6B; towards the margins, close to 6C; towards the base, close to 35C; with development, color towards the margins becomes closer to 7A to 7C. Lateral petals: Close to 35B; with development, color becomes closer to 51A to 51B. Lower keel: Close to 195C; towards the apex, close to 176A; apex, close to 177A; color does not change with development.

*Sepals.*—Quantity per flower: Two. Length: About 6 mm. Width: About 5.5 mm. Shape: Ovate. Apex: Acute. Base: Cuneate. Margin: Entire. Texture, upper and lower surfaces: Densely pubescent. Color, when opening, upper and lower surfaces: Close to 143C. Color, fully opened, upper and lower surfaces: Close to 146B to 146C.

*Peduncles.*—Length: About 37.7 cm. Diameter: About 7 mm. Strength: Strong. Aspect: Mostly erect. Texture: Smooth, glabrous. Color: Close to 183D.

*Pedicels*.—Length: About 1.3 cm. Diameter: About 1 mm. Strength: Moderately strong. Aspect: About 80° from peduncle axis Texture: Smooth, glabrous. Color: Close to 183C to 183D.

*Reproductive organs*.—Androecium: Quantity per flower: About ten. Filament length: About 4 mm to 7 mm. Filament color: Close to 144B to 144C. Anther shape: Narrowly oblong. Anther length: About 2 mm. Anther color: Close to 169B to 169D. Amount of pollen: Moderate to abundant. Pollen color: Close to 24A. Gynoecium: Quantity per flower: One. Pistil length: About 1.3 cm. Style length: About 1.25 cm. Style color: Close to 150D. Stigma shaped: Club-shaped, fringed. Stigma color: Close to 145D. Ovary color: Close to 144C to 144D.

*Fruits*.—Quantity per flower: One. Length: About 4.5 cm. Diameter: About 1 cm. Texture: Densely pubescent. Color: Close to 165A.

*Seeds*.—Quantity per fruit: About ten. Length: About 5 mm. Diameter: About 2 mm. Color: Close to 200A.

Garden performance: Plants of the new Lupine have been observed to have good garden performance and to tolerate rain, wind, high temperatures of about 35° C. and to be hardy to USDA Hardiness Zone 5.

Pathogen & pest resistance: Plants of the new Lupine have not been observed to be resistant to pathogens and pests common to Lupine plants.

It is claimed:

1. A new and distinct Lupine plant named 'Gladiator' as illustrated and described.

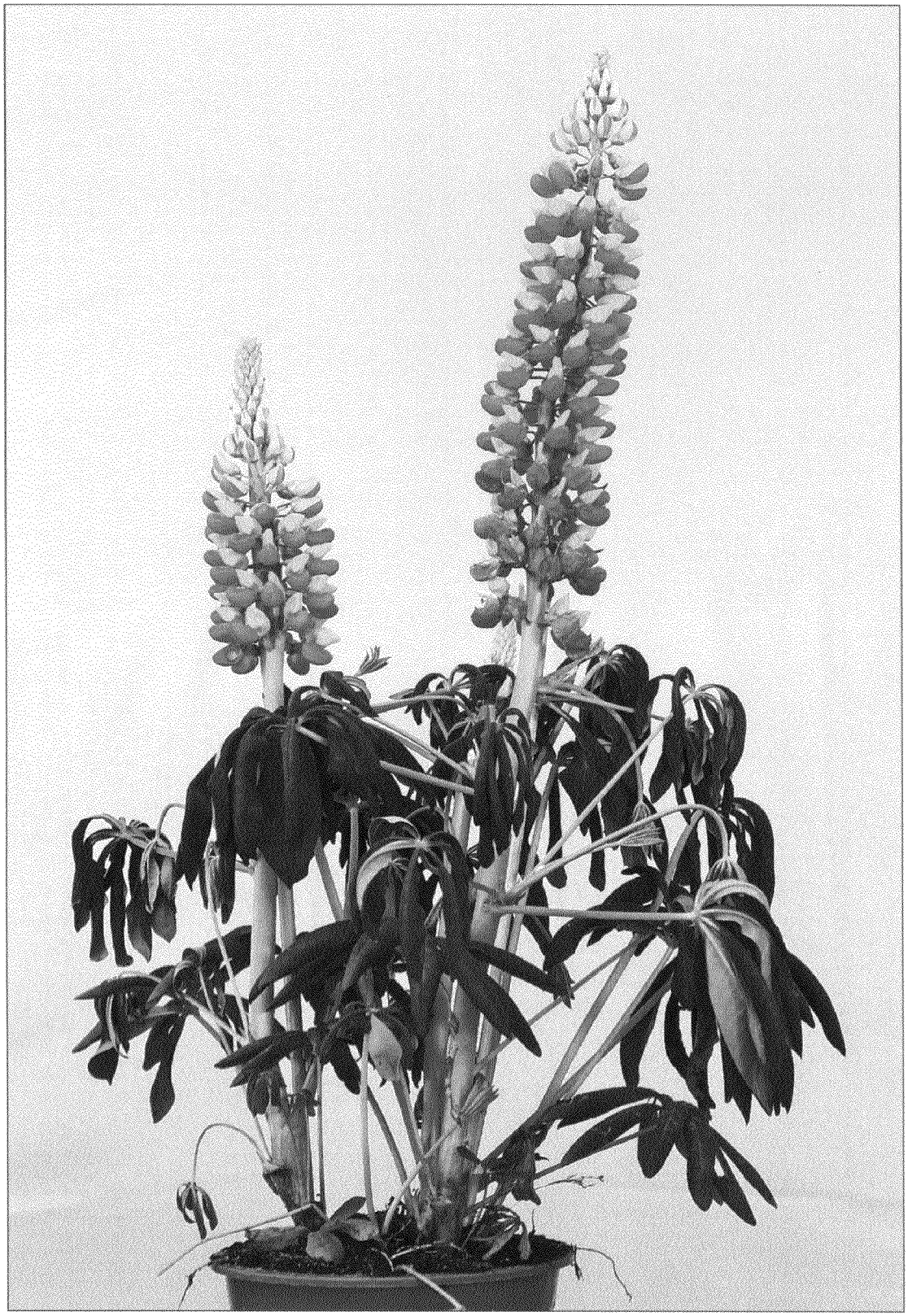

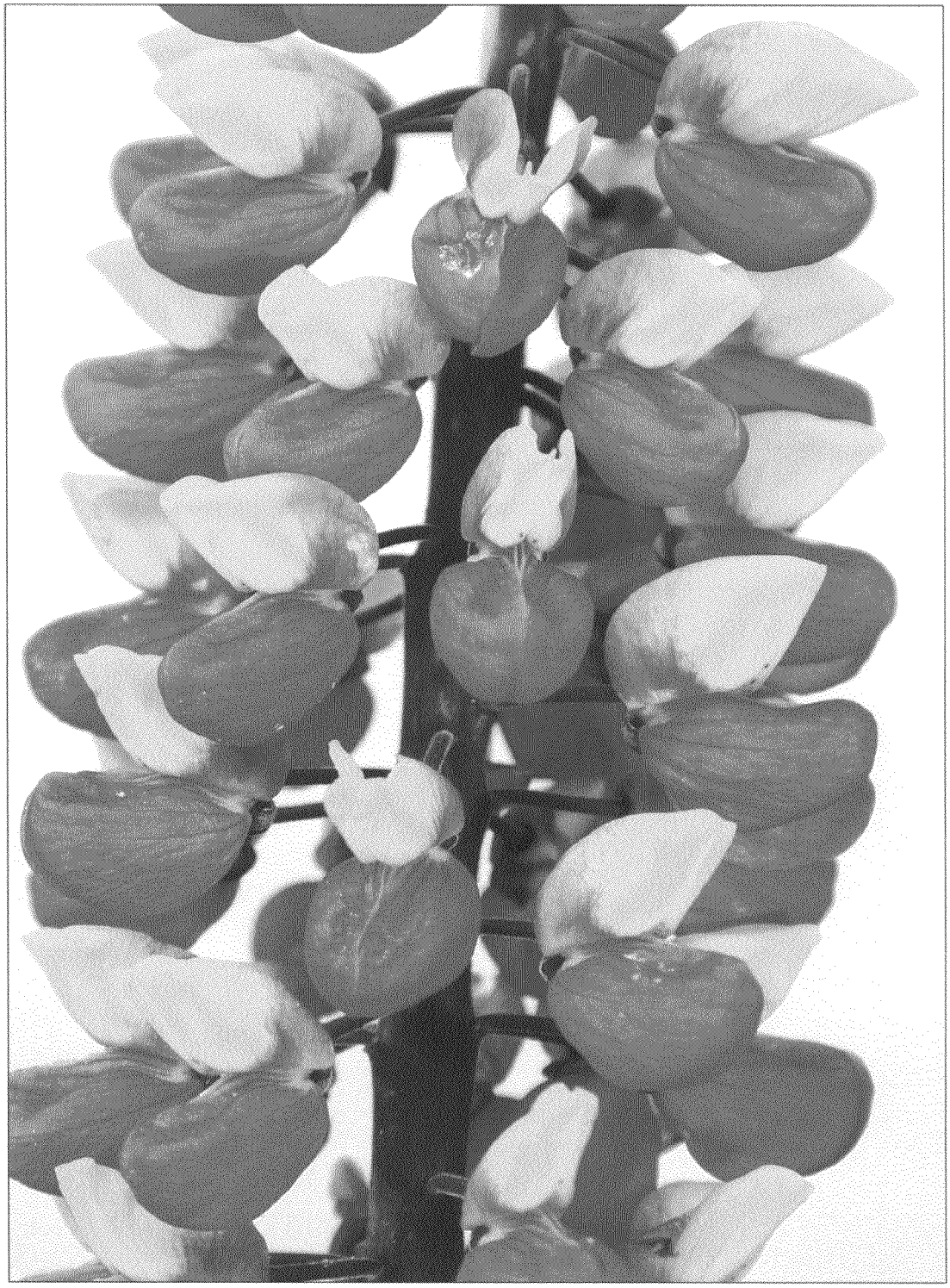

* * * * *